(12) United States Patent
Malkowski

(10) Patent No.: US 9,351,751 B2
(45) Date of Patent: May 31, 2016

(54) SWINGING BARS WITH AXIAL WHEELS TO DRIVE ARTICULATING CABLES

(75) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 354 days.

(21) Appl. No.: 13/543,913

(22) Filed: Jul. 9, 2012

(65) Prior Publication Data

US 2013/0012929 A1 Jan. 10, 2013

Related U.S. Application Data

(60) Provisional application No. 61/505,602, filed on Jul. 8, 2011.

(51) Int. Cl.
*A61B 1/005* (2006.01)
*A61B 17/00* (2006.01)
*A61B 17/29* (2006.01)

(52) U.S. Cl.
CPC .............. *A61B 17/29* (2013.01); *A61B 1/0052* (2013.01); *A61B 2017/003* (2013.01); *A61B 2017/00323* (2013.01); *A61B 2017/00327* (2013.01); *A61B 2017/2929* (2013.01)

(58) Field of Classification Search
None
See application file for complete search history.

(56) References Cited

U.S. PATENT DOCUMENTS

| | | | | |
|---|---|---|---|---|
| 3,572,325 A * | 3/1971 | Bazell et al. | ................... | 600/141 |
| 3,605,725 A * | 9/1971 | Bentov | ........................... | 600/434 |
| 4,294,233 A * | 10/1981 | Takahashi | .................... | 600/149 |
| 4,483,326 A * | 11/1984 | Yamaka et al. | ............... | 600/149 |
| 4,721,099 A * | 1/1988 | Chikama | ....................... | 600/152 |
| 4,886,067 A | 12/1989 | Palermo | | |
| 4,947,827 A * | 8/1990 | Opie | .................... | A61B 1/0052 600/108 |
| 5,325,845 A * | 7/1994 | Adair | ........................... | 600/114 |
| 5,326,013 A * | 7/1994 | Green | ............. | A61B 17/07207 227/176.1 |
| 5,330,502 A * | 7/1994 | Hassler et al. | ................ | 606/205 |
| 5,409,498 A * | 4/1995 | Braddock et al. | ............. | 606/143 |
| 5,472,017 A | 12/1995 | Kovalcheck | | |
| 5,676,653 A * | 10/1997 | Taylor et al. | ............... | 604/95.04 |
| 5,762,069 A * | 6/1998 | Kelleher et al. | ............... | 600/564 |
| 5,785,647 A * | 7/1998 | Tompkins et al. | ........... | 600/201 |
| 5,904,667 A * | 5/1999 | Falwell | ...................... | 604/95.01 |
| 5,938,616 A * | 8/1999 | Eaton | ................... | A61B 1/0052 600/446 |
| 5,954,654 A * | 9/1999 | Eaton | ................... | A61B 1/0052 600/459 |
| 6,162,208 A * | 12/2000 | Hipps | ............................. | 606/1 |
| 2005/0277874 A1* | 12/2005 | Selkee | ....................... | 604/95.04 |
| 2006/0142732 A1* | 6/2006 | Karmarkar et al. | ........... | 604/508 |
| 2006/0252993 A1* | 11/2006 | Freed et al. | .................... | 600/146 |
| 2007/0021737 A1* | 1/2007 | Lee | .................................. | 606/1 |
| 2007/0221701 A1* | 9/2007 | Ortiz | .................... | A61B 17/068 227/175.1 |
| 2007/0255102 A1* | 11/2007 | Maruyama | .................... | 600/146 |
| 2008/0097476 A1* | 4/2008 | Peh et al. | ....................... | 606/130 |
| 2008/0188868 A1 | 8/2008 | Weitzner et al. | | |

(Continued)

*Primary Examiner* — Lynsey Crandall
*Assistant Examiner* — Manolis Pahakis

(57) ABSTRACT

Disclosed is an articulation mechanism for a surgical instrument including a housing defining a longitudinal axis. The housing has a first slot extending at least partially through the housing and a second slot extending at least partially through the housing offset from the first slot. The articulation mechanism further includes a first bar member which is adapted for insertion into the first slot. The articulation mechanism further includes a second bar member which is adapted for insertion into the second slot. Each bar member is rotatable within its respective slot to articulate a cable. Each end portion of each bar member includes a pulley inserted into a channel of the end portion which is adapted for the engagement with a cable.

9 Claims, 12 Drawing Sheets

(56) References Cited

U.S. PATENT DOCUMENTS

| | | |
|---|---|---|
| 2008/0188869 A1 | 8/2008 | Weitzner et al. |
| 2008/0312506 A1* | 12/2008 | Spivey ............... A61B 1/00138 600/149 |
| 2009/0065549 A1* | 3/2009 | Viola ......................... 227/175.1 |
| 2009/0090764 A1* | 4/2009 | Viola ......................... 227/176.1 |
| 2009/0187185 A1* | 7/2009 | Lyons et al. .................... 606/41 |
| 2009/0216245 A1* | 8/2009 | Viola ............................ 606/108 |
| 2009/0312773 A1* | 12/2009 | Cabrera et al. ................ 606/144 |
| 2010/0004633 A1 | 1/2010 | Rothe et al. |
| 2010/0069834 A1* | 3/2010 | Schultz ...................... 604/95.04 |
| 2010/0121147 A1 | 5/2010 | Oskin et al. |
| 2010/0168827 A1* | 7/2010 | Schultz ......................... 607/116 |
| 2010/0193568 A1* | 8/2010 | Scheib ............ A61B 17/07207 227/176.1 |
| 2011/0144576 A1* | 6/2011 | Rothe et al. ................. 604/95.04 |
| 2011/0208211 A1* | 8/2011 | Whitfield et al. ............. 606/142 |
| 2011/0230875 A1* | 9/2011 | Walberg ................ A61B 17/29 606/33 |
| 2012/0078243 A1* | 3/2012 | Worrell et al. ................... 606/33 |
| 2012/0080500 A1* | 4/2012 | Morgan ........... A61B 17/00234 227/179.1 |
| 2012/0109186 A1* | 5/2012 | Parrott et al. .................. 606/206 |
| 2012/0253326 A1* | 10/2012 | Kleyman ........... A61B 19/2203 606/1 |
| 2013/0023868 A1* | 1/2013 | Worrell et al. ................... 606/33 |

* cited by examiner

SWINGING BARS WITH AXIAL WHEELS TO DRIVE ARTICULATING CABLES

CROSS-REFERENCE TO RELATED APPLICATIONS

This application claims the benefit of and priority to U.S. Provisional Patent Application No. 61/505,602, filed Jul. 8, 2011, the entire disclosure of which is incorporated by reference herein.

BACKGROUND

1. Technical Field

The present disclosure relates generally to articulation of laparoscopic instruments. More particularly, the present disclosure relates to the use rotating knobs and swinging bars to control and articulate the distal end of a surgical articulation apparatus.

2. Description of Related Art

Increasingly, many surgical procedures are performed through small openings in the skin. As compared to the larger openings typically required in traditional procedures, smaller openings result in less trauma to the patient. By reducing the trauma to the patient, the time required for recovery is also reduced. Generally, the surgical procedures that are performed through small openings in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through an opening in tissue. A surgeon is generally required to manipulate a surgical articulation apparatus through the use of a series of knobs or other control mechanisms to perform a surgical operation.

SUMMARY

Disclosed herein is an articulation mechanism for a surgical instrument which includes a set of axially swinging bars and rotating knobs for articulating an articulatable section of a surgical instrument.

The articulation mechanism includes a housing defining a longitudinal axis. The housing has a first slot extending at least partially through the housing and a second slot extending at least partially through the housing offset from the first slot. The articulation mechanism further includes a first bar member which is adapted for insertion into the first slot. The first bar member is rotatable within the first slot about a first axis to articulate a first cable and has a first end portion and a second end portion. Each end portion of the first bar member includes a pulley inserted into a channel of the end portion which is adapted for the engagement with a cable. The articulation mechanism further includes a second bar member which is adapted for insertion into the second slot. The second bar member is rotatable within the second slot about a second axis to articulate a second cable and has a first end portion and a second end portion. Each end portion of the second bar member includes a pulley inserted into a channel of the end portion which is adapted for engagement with a cable.

The articulation mechanism further includes a rotating member which is rotatable about the longitudinal axis and defines a passageway extending therethrough for the reception of the housing. The passageway defines an internal thread which is adapted for engagement with at least one of the first and second end portions of one of the first and second bar members. The internal thread is adapted to rotate the one of the first and second bar members within the respective first or second slot.

The articulation mechanism may further include a spacing member defining an opening extending therethrough for the reception of the housing which is adapted limit movement of the rotating member in an axial direction relative to the longitudinal axis. The spacing member may include a plurality of flanged portions and each flanged portion may define at least one hole therethrough for the reception of a cable. The housing may include a plurality of grooved channels extending along an outer surface which are adapted to receive at least a portion of the plurality of flanged portions of the spacing member.

Each bar member may define a tapered section along one of the first and second end portions and each bar member may include a rounded tip extending from one of the first and second end portions which is adapted for engaging the internal thread of the rotating member. The first and second bar members may each include a nub extending therefrom for engagement with the first and second slots respectively where the first and second bar members are each rotatable about their respective nubs.

In another embodiment of the present disclosure, an articulation mechanism for a surgical instrument is disclosed including a housing defining a longitudinal axis. The housing has a first slot extending at least partially through a side of the housing and a second slot extending at least partially through the side of the housing offset from the first slot. The articulation mechanism further includes a first bar member which is adapted for insertion into the first slot. The first bar member is rotatable within the first slot about a first axis to articulate a first cable secured thereto. The articulation mechanism further includes a second bar member which is adapted for insertion into the second slot and rotatable within the second slot about a second axis to articulate a second cable secured thereto.

The articulation mechanism further includes a rotating member which is rotatable about the longitudinal axis and which defines a passageway extending therethrough for the reception of the housing. The passageway defines an internal thread which is adapted for engagement with at least one end portion of one of the first and second bar members where the internal thread is adapted to rotate the one of the first and second bar members within the respective first or second slot. At least one end portion of each bar member defines a tapered section and at least one end portion of each bar member includes a rounded tip which is adapted for engaging the internal thread of the rotating member. Each cable may be secured to one of the bar members by a ferrule and the first and second bar members may each include a nub extending therefrom for engagement with the first and second slots respectively where the first and second bar members are each rotatable about their respective nubs.

In another embodiment of the present disclosure a surgical articulation system is disclosed including a handle assembly, having a grip and a lever, and an articulation mechanism extending from the handle assembly. The articulation mechanism includes a housing defining a longitudinal axis. The housing has a first slot extending at least partially through the housing and a second slot extending at least partially through the housing offset from the first slot. The articulation mechanism further includes a first bar member which is adapted for insertion into the first slot and rotatable within the first slot about a first axis. The articulation mechanism further includes a second bar member which is adapted for insertion into the second slot and rotatable within the second slot about a second axis. The surgical articulation system further includes an elongate member extending distally from the articulation mechanism and having at least one articulatable section which is operatively associated with the first and second bar members by a plurality of cables extending therebetween. The surgical articulation system also includes an end effector extending from the elongate member and actuatable by the handle assembly.

The surgical articulation system may further include a rotating member which is rotatable about the longitudinal axis and which defines a passageway extending therethrough for the reception of the housing. The passageway defines an internal thread which is adapted for engagement with at least one end portion of one of the first and second bar members where the internal thread is adapted to rotate the one of the first and second bar members within one of the respective first or second slot.

Rotation of the first bar member articulates the articulatable section of the elongate member in a first direction and rotation of the second bar member articulates the articulatable section of the elongate member in a second direction. Each bar member may include a pulley inserted into a channel defined therein for engaging one of the plurality of cables. At least one end portion of each bar member may also define a tapered section and at least one end portion of each bar member includes a rounded tip which is adapted for engaging the internal thread of the rotating member.

BRIEF DESCRIPTION OF THE DRAWINGS

The accompanying drawings, which are incorporated in and constitute a part of this specification, illustrate embodiments of the presently disclosed surgical articulation system, and together with a general description of the presently disclosed surgical articulation system given above, and the detailed description of the embodiments given below, serve to explain the principles of the presently disclosed surgical articulation system.

DETAILED DESCRIPTION

Figure 1:
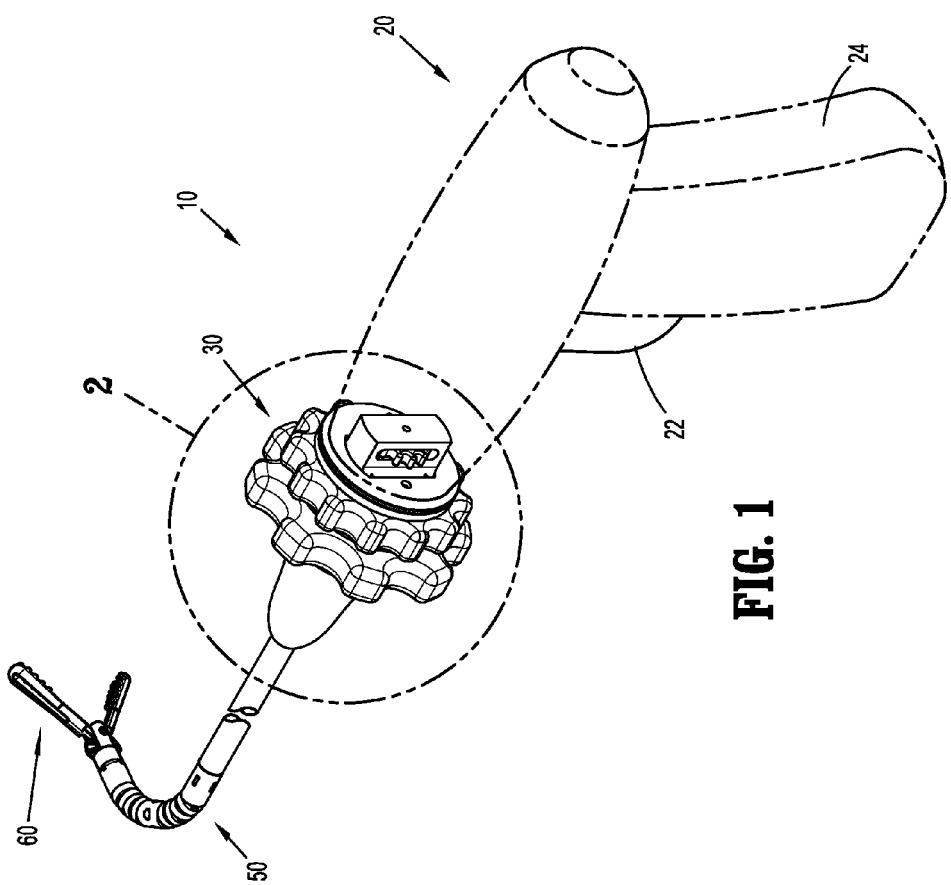
FIG. 1 is a perspective view of a surgical articulation system in accordance with the present disclosure.
Figure 2:
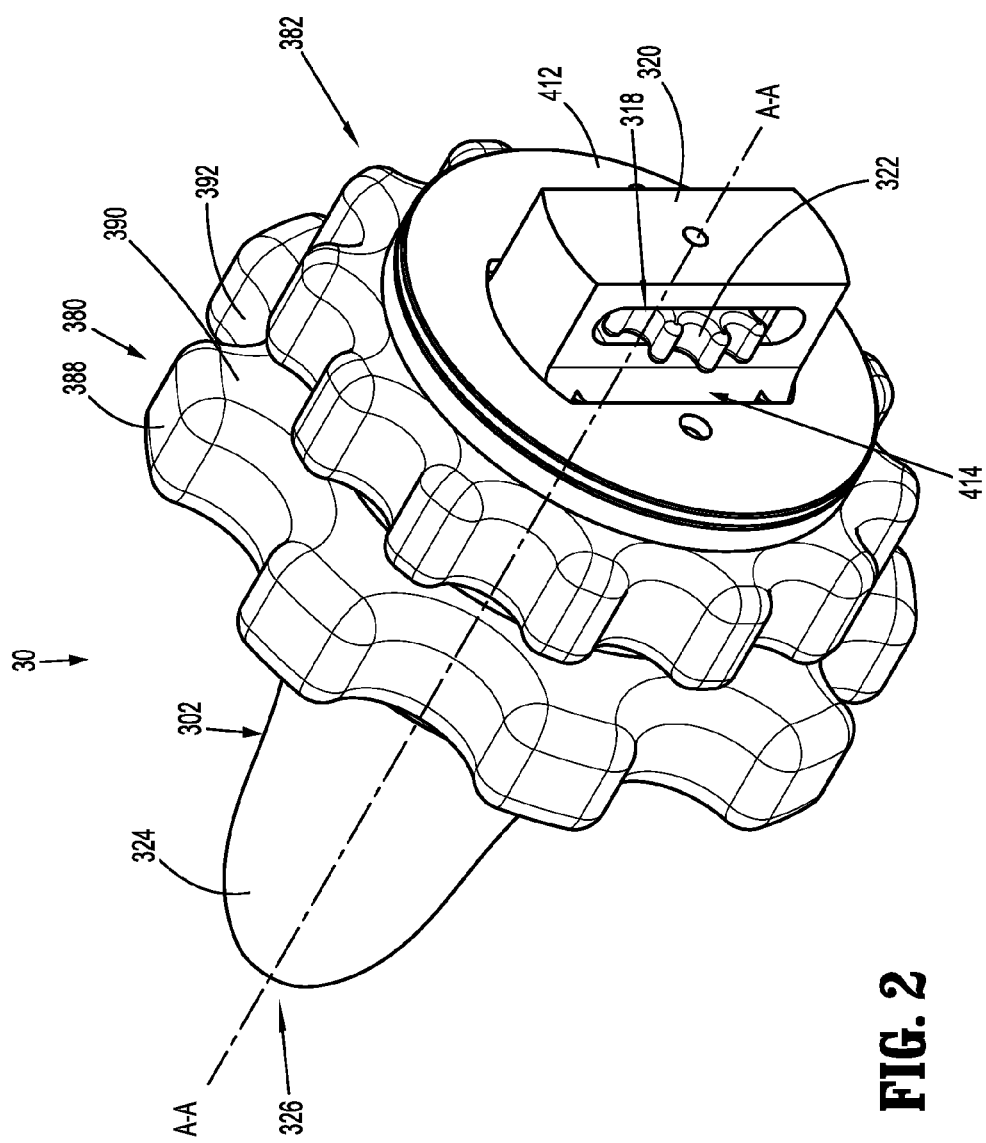
FIG. 2 is a perspective view of the articulation mechanism of the surgical articulation system of FIG. 1.
Figure 3:
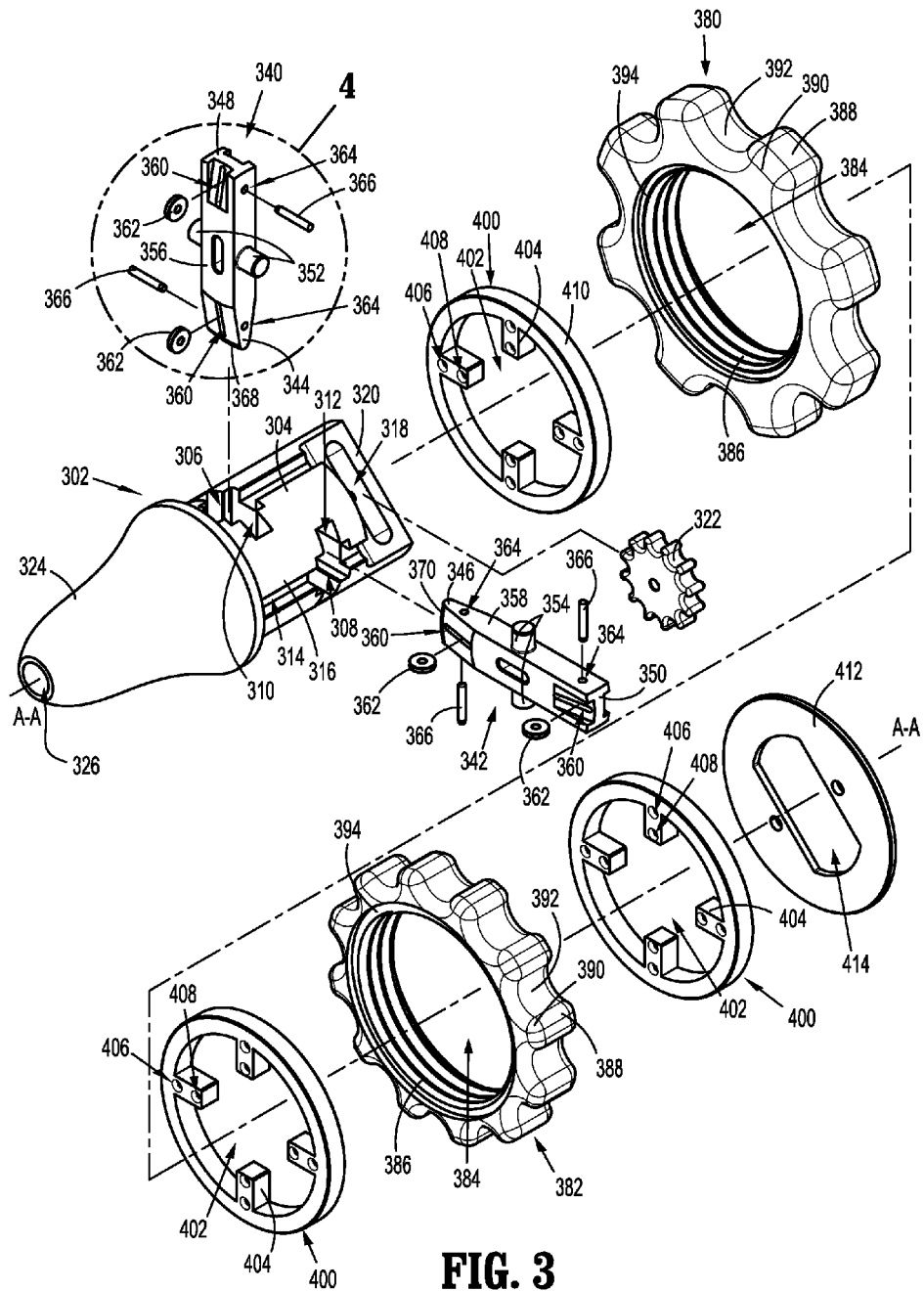
FIG. 3 is an exploded view of the articulation mechanism of FIG. 2.
Figure 6:
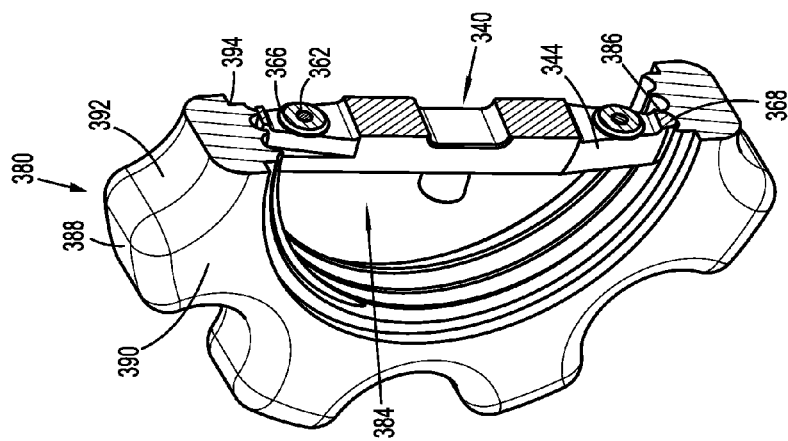
FIG. 6 is a cross-sectional view taken along section line 6-6 of FIG. 5.
Figure 5:
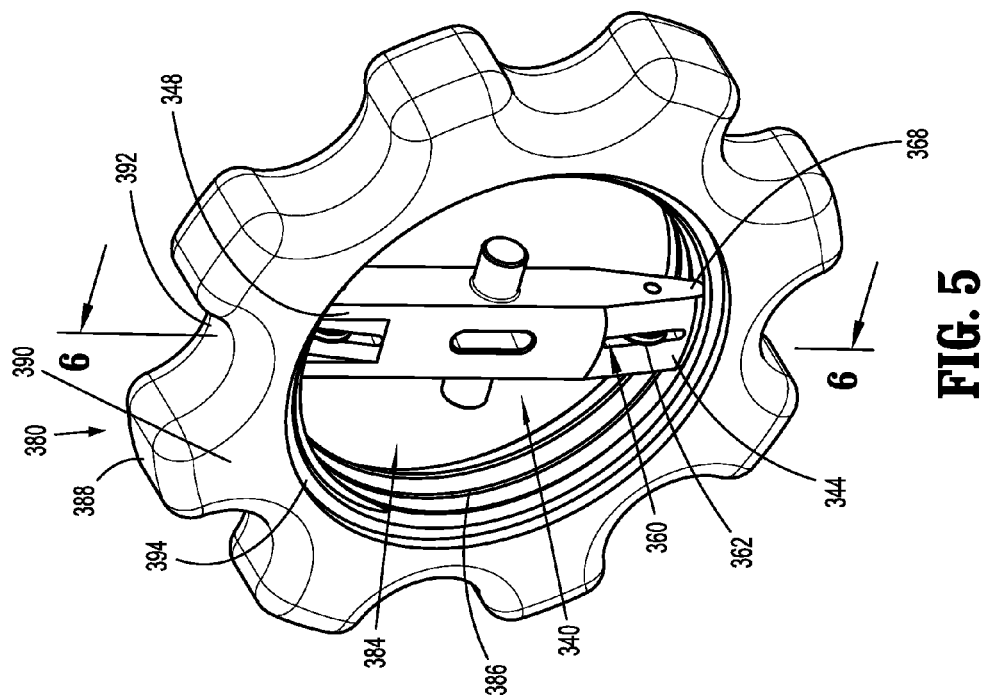
FIG. 5 is a perspective view of one of the bar members of FIG. 3 engaged with one of the rotating members of FIG. 3.
Figure 4:
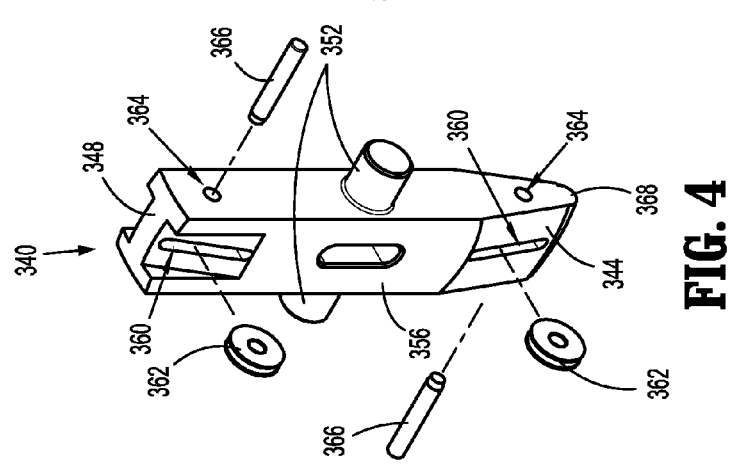
FIG. 4 is an perspective view of one of the bar members of FIG. 3.
Figure 7:
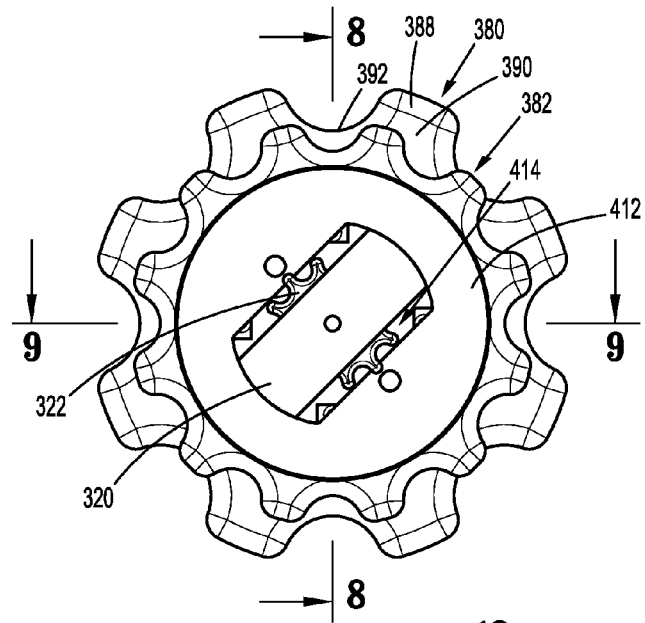
FIG. 7 is a rear view of the articulation mechanism of FIG. 2.
Figure 8:
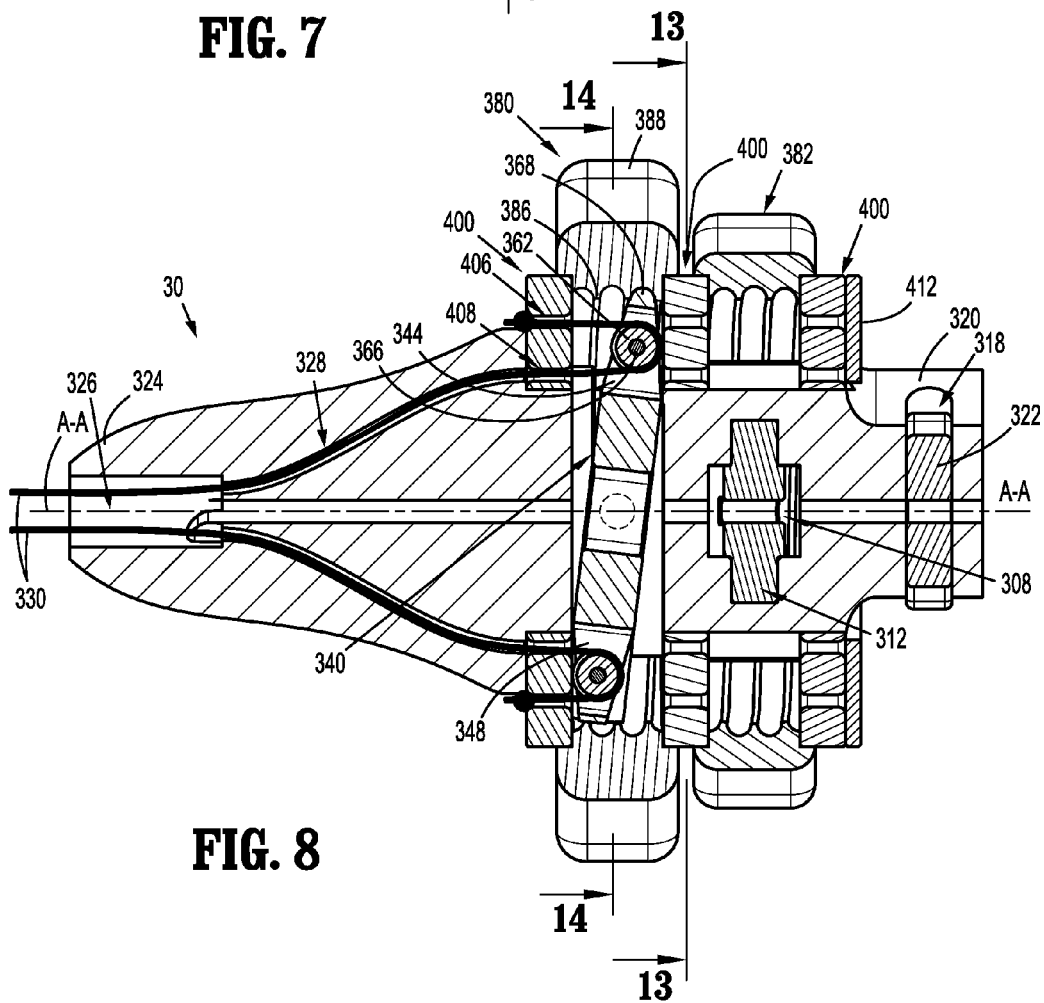
FIG. 8 is a cross-sectional view taken along section line 8-8 of FIG. 7 showing the first bar member.
Figure 9:
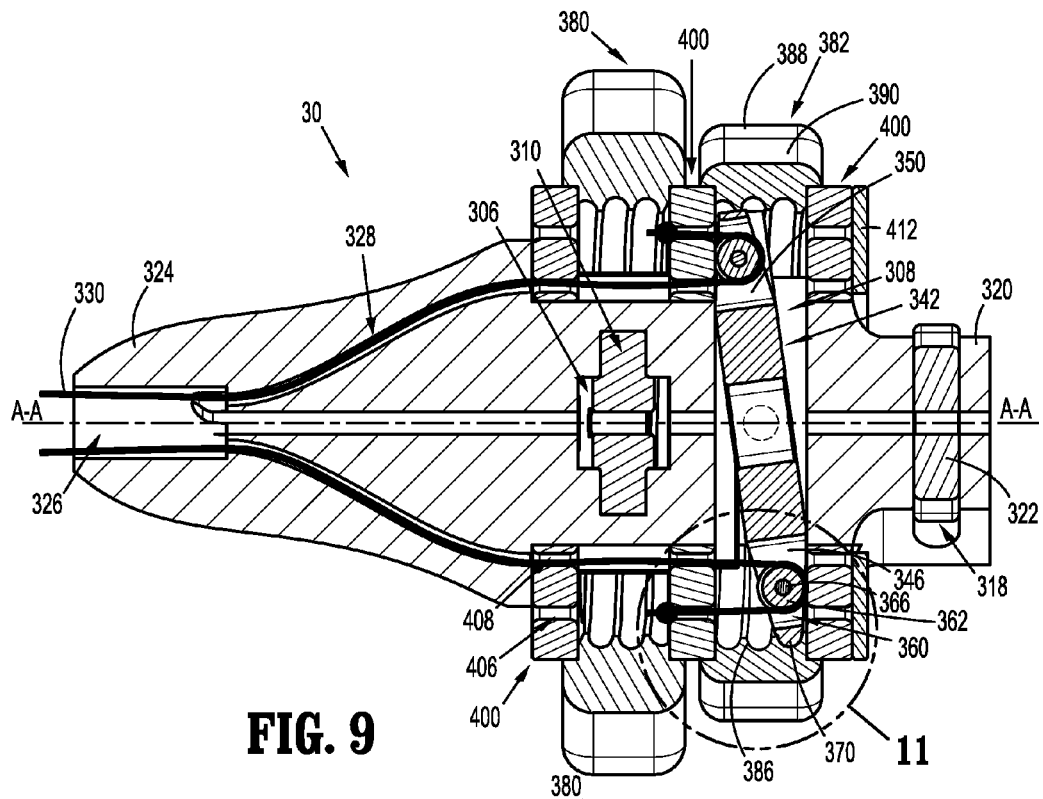
FIG. 9 is a cross-sectional view taken along section line 9-9 of FIG. 7 showing the second bar member.
Figure 10:
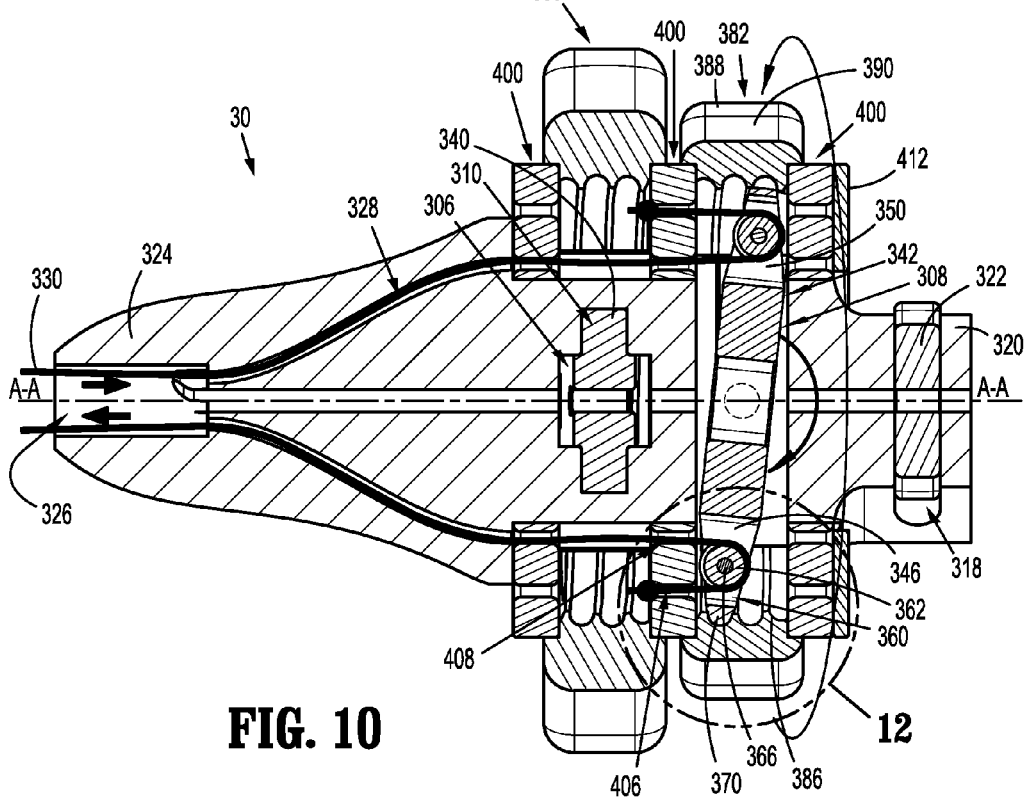
FIG. 10 is view of FIG. 9 showing the second bar member after the rotating member has been rotated.
Figure 11:
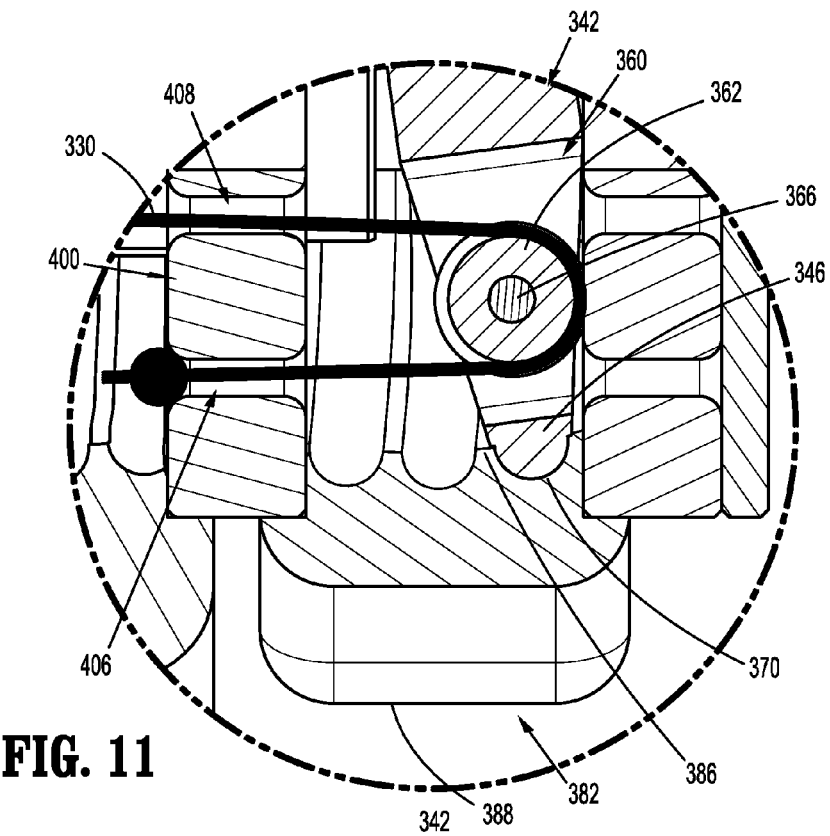
FIG. 11 is a detailed view of the section of detail indicated in FIG. 9 showing the bar member in a first position prior to rotation of the rotating member.
Figure 12:
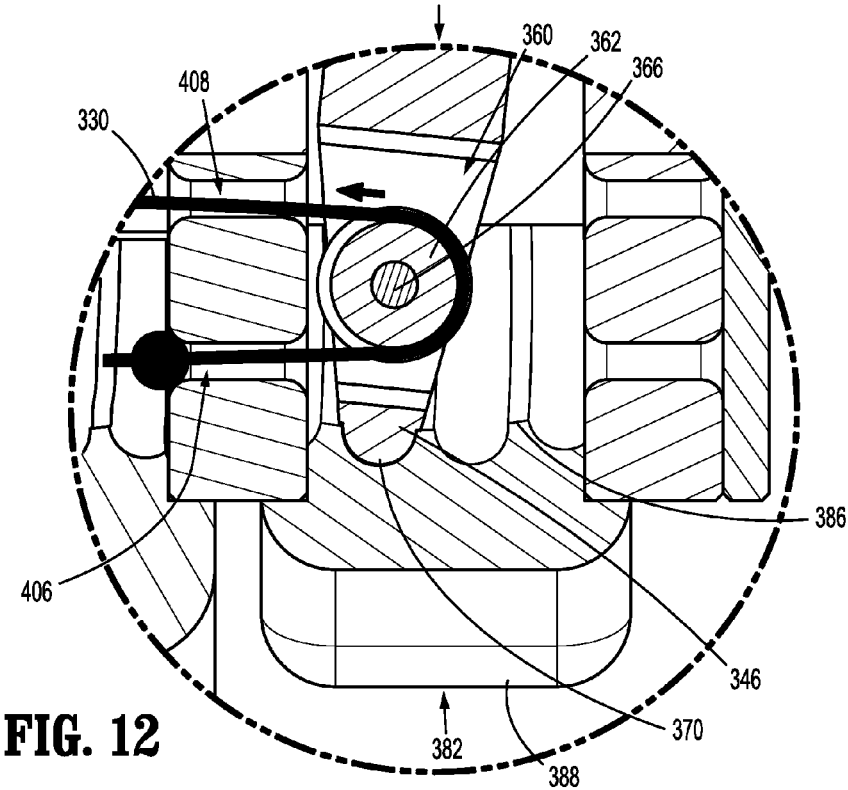
FIG. 12 is a detailed view of the section of detail indicated in FIG. 10 showing the bar member in a second position after rotation of the rotating member.
Figure 13:
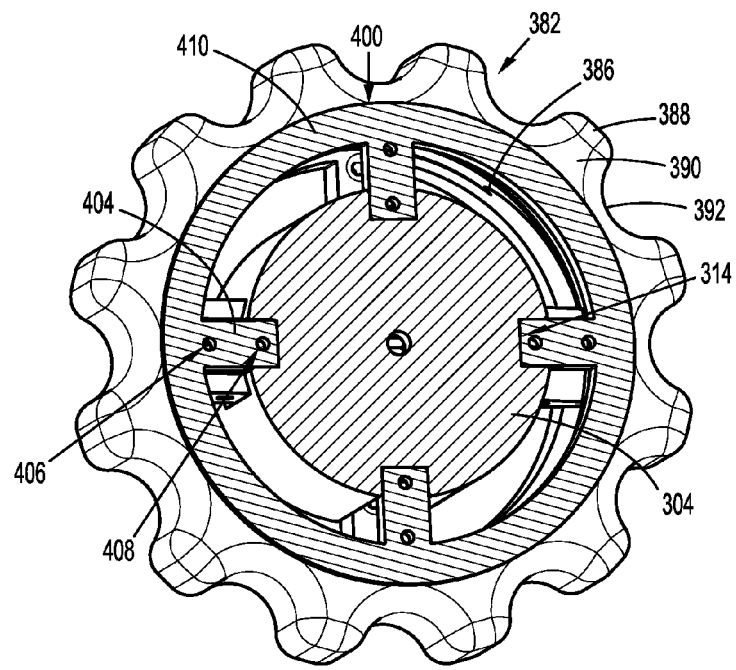
FIG. 13 is a cross-sectional view taken along section line 13-13 of FIG. 8 showing a spacing member aligned with the grooved channels of the housing.
Figure 14:
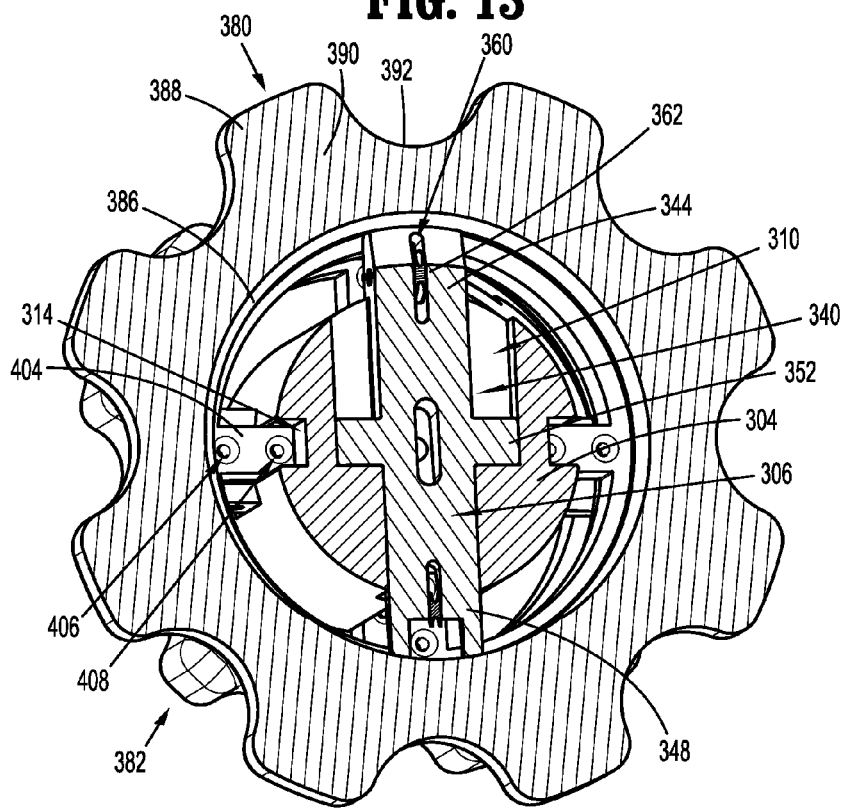
FIG. 14 is a cross-sectional view taken along section line 14-14 of FIG. 8 showing the nubs of the bar member engaged with the slot of the housing.
Figure 15:
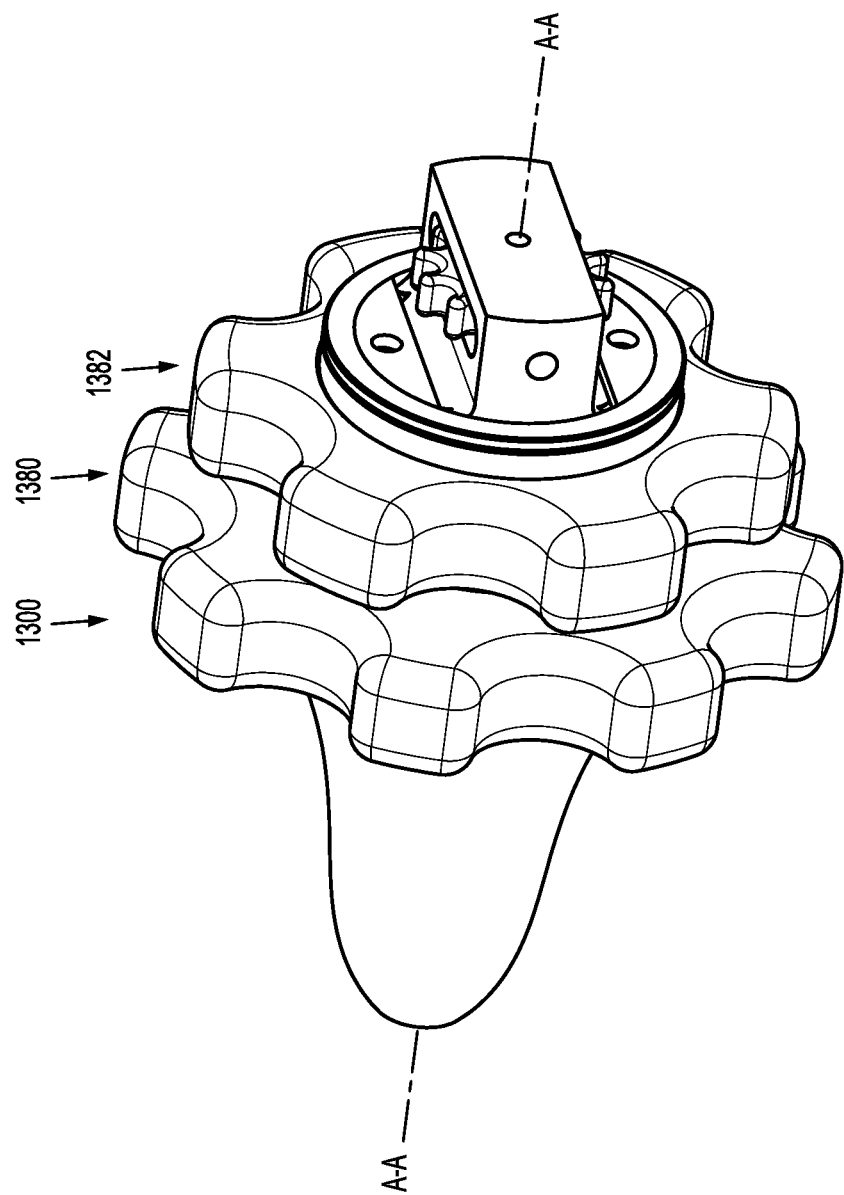
FIG. 15 is a perspective view of a articulation mechanism according to another embodiment of the present disclosure.
Figure 16:
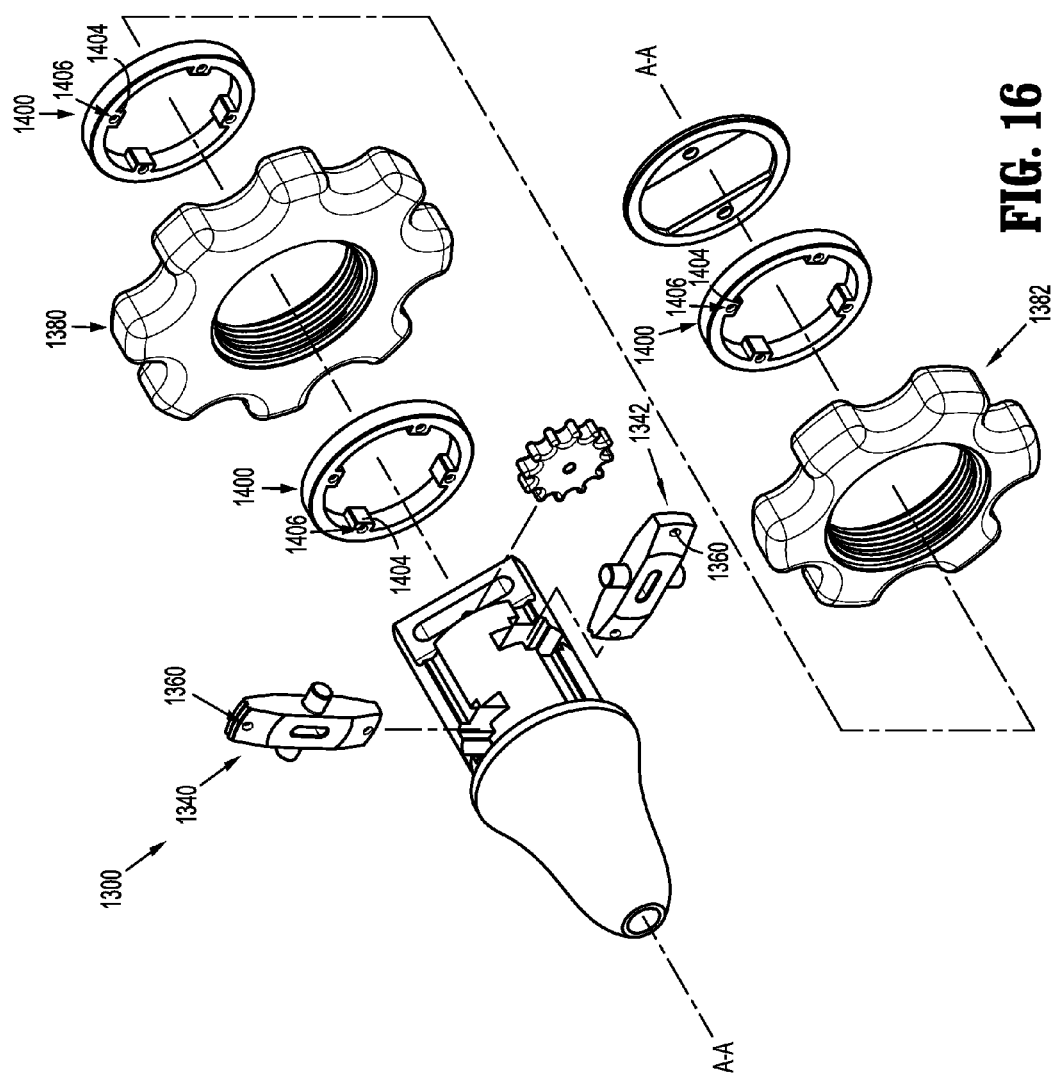
FIG. 16 is an exploded view of the articulation mechanism of FIG. 15.
Figure 17:
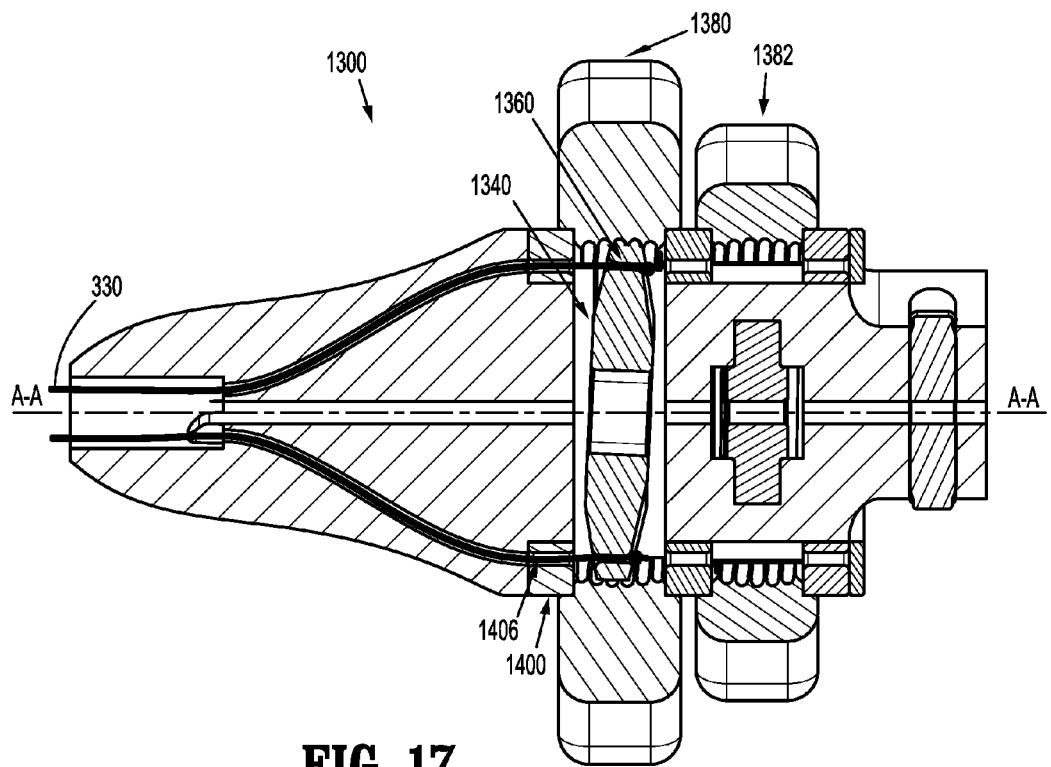
FIG. 17 is a side cross-sectional view of the articulation mechanism of FIG. 15 showing the first bar member having a cable secured thereto.
Figure 18:
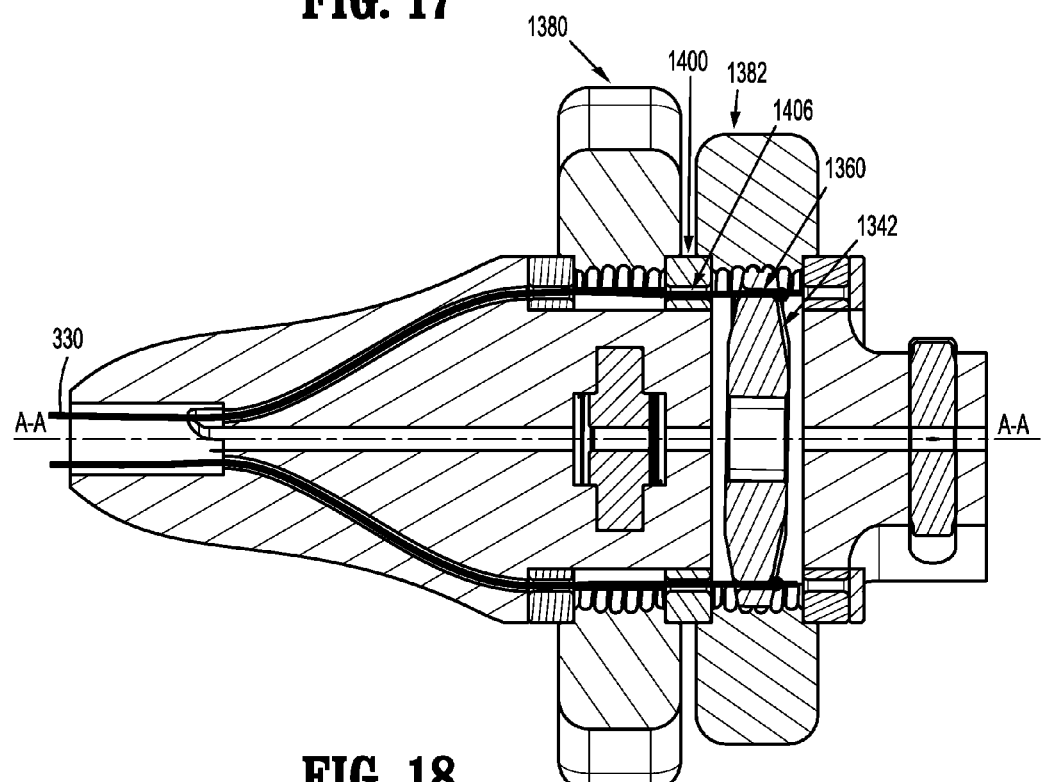
FIG. 18 is a side cross-sectional view of the articulation mechanism of FIG. 15 showing the second bar member having a cable secured thereto.

Disclosed herein is a surgical articulation mechanism which provides for a way of articulating a distal end of a surgical instrument through the use of rotating members and axially swinging bars.

Particular embodiments of the presently disclosed surgical articulation apparatus are described in detail with reference to the drawing figures wherein like reference numerals identify similar or identical elements. As used herein, the term "distal" refers to that portion which is farther from the user while the term "proximal" refers to that portion which is closer to the user or surgeon.

With reference to FIG. 1, a surgical articulation system 10 is disclosed including a handle assembly 20, an articulation mechanism 30 at a distal end of the handle assembly 20, an articulatable member 50 extending distally from articulation mechanism 30 and an end effector 60 at a distal end of the articulatable member 50.

Handle assembly 20 includes a lever 22 and a grip 24. Lever 22 is operatively associated with end effector 60 and actuatable to actuate end effector 60 to perform a surgical operation. End effector 60 may be any kind of end effector suitable for surgical use including cutting devices, sealing devices, grasping devices, optical devices or any other surgical device requiring articulation. Lever 22 may mechanically actuate end effector 60 or may actuate an electric motor or other electronic component (not shown) to actuate end effector 60.

Referring now to FIGS. 2-14, articulation mechanism 30 will be described. Articulation mechanism 30 includes a housing 302 including an elongate portion 304 having a first slot 306 and a second slot 308. As seen in FIGS. 3 and 8-10, slots 306 and 308 extend at least partially through elongate portion 304 transverse to a longitudinal axis A-A of housing 302. Slot 308 is offset from slot 306 both axially and circumferentially. Each slot 306 and 308 also defines a notched portion 310 and 312 respectively which extends partially through elongate portion 304. Notched portions 310 and 312 may, for example, extend only half way through elongate portion 304. Elongate portion 304 also includes grooved channels 314 extending along an outer surface 316 in the axial direction and may also include an opening 318 in a proximal portion 320 for the reception of a knob 322 which is operatively associated with end effector 60 to rotate end effector 60 about its longitudinal axis. Housing 302 also includes a distal portion 324 having a distal opening 326 and cable pathways 328 extending proximally from distal opening 326 for the reception of cables 330 therethrough. More slots may also be included as desired for increased articulation capability.

Referring now to FIGS. 3-8 and 14, each slot 306 and 308 is adapted to receive a bar member 340 and 342 respectively. Each bar member 340 and 342 is adapted for insertion into slots 306 and 308 such that end portions 344, 346, 348, and 350 extend out of slots 306 and 308. Each bar member 340 and 342 also includes a nub 352 and 354 respectively disposed on central portions 356 and 358. Nubs 352 and 354 are inserted into notched portions 310 and 312 respectively when bar members 340 and 342 are inserted into slots 306 and 308 to limit the radial motion of bar members 340 and 342 relative to elongate portion 304 and to allow bar members 340 and 342 to rotate about nubs 352 and 354 when in slots 306 and 308. Each end portion 344, 346, 348 and 350 includes a pulley opening 360 extending therethrough for the reception of a pulley 362 and a pin opening 364 extending therethrough transverse to pulley opening 360 for the reception of a pin 366. Pin 366 is inserted into pin opening 364 to secure pulley 362 within pulley opening 360. Pulley 362 is adapted to engage one of cables 330 to allow for articulation of articulatable member 50 by rotation of bar members 340 and 342 as will be described in further detail below with regard to the cable routing. End portions 344 and 346 of bar members 340 and 342 are generally tapered to rounded tips 368 and 370 while end portions 348 and 350 are not tapered. Alternatively end portions 348 and 350 may also be tapered and may also include rounded tips.

Referring now to FIGS. 3-6, articulation mechanism 30 further includes rotating members 380 and 382 corresponding to bar members 340 and 342 respectively. Each rotating member 380 and 382 includes an opening 384 extending therethrough having an internal thread 386 and tactile protrusions 388 on an outer surface 390. Tactile protrusions 388 provide a surgeon with tactile feedback when manipulating rotating members 380 and 382 and include arcuate depressions 392 dimensioned for comfortable reception of a surgeons finger. Opening 384 of each rotating member 380 and 382 is adapted for reception of elongate portion 304 therethrough and internal thread 386 is adapted to engage rounded tips 368 and 370 of bar members 340 and 342 respectively such that upon rotation of rotating members 380 and 382 about longitudinal axis A-A rounded tips 368 and 370 traverse internal thread 386. As rounded tips 368 and 370 traverse internal thread 386, bar members 340 and 342 are rotated within slots 306 and 308 about nubs 352 and 354 respectively. Rotating members 380 and 382 may define a circular or ring like shape or may alternatively define other shapes suitable for manipulation by a surgeon including but not limited to, for example, squares, triangles, rectangles, or other polygonal shapes. Rotating members 380 and 382 having internal threads 386 with a larger or smaller pitch may be provided if the surgeon desires finer or coarser control of the articulatable member. The tactile protrusions 388 of rotating member 382 may be smaller or larger than those found on rotating member 380 to provide a surgeon with a noticeable difference between rotating members 380 and 382. Tactile protrusions 388 of rotating member 382 may also be smaller than those found on rotating member 380 to provide a surgeon with easier access to rotating member 380 when gripping handle 24.

Referring now to FIGS. 3, 8-10 and 13-14, rotating members 380 and 382 are held axially in place by spacing members 400. Each spacing member 400 includes an opening 402 extending therethrough for the reception of elongate portion 304 of housing 302 and includes a plurality of flanges 404 extending radially inward into opening 402. The plurality of flanges 404 is adapted to engage grooved channels 314 of elongate portion 304. In the present embodiment each spacing member 400 includes four flanges 404 but there may alternatively be any number of flanges 404 including, for example, no flanges 404, one flange 404, two flanges 404, or more flanges 404. When flanges 404 are engaged with grooved channels 314 spacing member 400 is prevented from rotating about longitudinal axis A-A. Spacing member 400 also includes cable holes 406 and 408 extending through each flange 404 for the reception of cables 330 therethrough. Where no flanges are provided cable holes 406 and 408 may instead extend through body portion 410 of spacing member 400. Body portion 410 is adapted to engage one or both of rotating members 380 and 382 to limit axial movement of rotating members 380 and 382 while still allowing rotational movement. Body portion 410 defines a generally circular shape and rotating members 380 and 382 define corresponding recesses 394 on either side of internal thread 386 for the reception of body portion 410. Body portion 410 and recesses 394 may alternatively be any shape suitable to allow rotating members 380 and 382 to rotate relative to body portion 410. In the present embodiment, three spacing members 400 are provided but any number of spacing members 400 may be provided depending on the number of rotating members 380 and 382, bar members 340 and 342 and slots 306 and 308. Spacing members 400 and rotating members 380 and 382 are held axially in place by an end plate 412. End plate 412 includes an opening 414 extending therethrough for the reception proximal portion 320 of elongate portion 304 and is securable to elongate portion 304 by a screw or other attachment means suitable for the purpose of securing end plate 412 to elongate portion 304. Once secured to elongate portion 304, end plate 412 limits axial movement of spacing members 400 and rotating members 380 and 382.

With reference to FIGS. 3, and 8-10 the assembly of articulation mechanism 30 will now be described. During assembly, cables 330 are routed through distal opening 326 and through cable pathways 328 of housing 302. In the present embodiment four cables 330 are shown however greater or fewer numbers of cables 330 may be used as needed. A first of the separating members 400 is engaged with grooved channels 314 of elongate portion 304 and moved distally along elongate portion 304 until it abuts a proximal face of distal portion 324. Cables 330 are then inserted through one of holes 406 and 408 of each flange 404 of the first of the spacing members 400. Bar member 340 is then inserted into first slot 304 until nubs 352 bottom out in notched portion 310. One of cables 330 is wound around each pulley 362 of bar member 340 before being inserted through the other of holes 406 and 408 of the respective flange 404 of the first of the spacing members 400 and secured to the other of holes 406 and 408. Cables 330 may be secured by a ferrule, welding, or other attachment means suitable to secure cables 330 to or against flanges 404. In this way two of cables 330 are attached on opposite sides of the first of spacing members 400 and operatively associated with first bar member 340.

Rotating member 380 is then slid distally onto elongate portion 304 until internal thread 386 engages bar member 340 and body portion 410 of the first of spacing members 400 engages recesses 394 on the distal side of rotating member 380. A second of the spacing members 400 is then engaged with grooved channels 314 and slid distally until body portion 410 of the second of the spacing members 400 engages recesses 394 on the proximal side of rotating member 380. In this way rotating member 380 is secured axially in place while still being able to rotate about the longitudinal axis A-A to rotate bar member 340 about nubs 352.

Each of the remaining two cables 330 is inserted through holes 406 and 408 of respective flanges 404 of the second of the spacing members 400 and bar member 342 is inserted into second slot 306 until nubs 354 bottom out in notched portion 312. One of the remaining cables 330 is wound around each pulley 362 of bar member 342 before being inserted through the other of holes 406 and 408 of the second of the spacing members 400 and secured to the other of holes 406 and 408 as described above. In this way two of cables 330 are attached on opposite sides of the second of spacing members 400 and operatively associated with second bar member 342.

Rotating member 382 is then slid distally onto elongate portion 304 until internal thread 386 engages bar member 342 and body portion 410 of the second of spacing members 400 engages recesses 394 on the distal side of rotating member 382. A third of the spacing members 400 is then engaged with grooved channels 314 and slid distally onto elongate portion 304 until body portion 410 of the third of the spacing members 400 engages recesses 394 on the proximal side of rotating member 382. In this way rotating member 382 is secured axially in place while still being able to rotate about the longitudinal axis A-A to rotate bar member 342 about nubs 354. Finally end plate 412 is slid distally onto proximal portion 320 until it abuts the third of the spacing members 400 and elongate portion 304 and is secured in place by a screw or other fastener. Articulation mechanism 30 is now secured together and ready for use. Although described in terms of assembly, the articulation mechanism 30 will come pre-assembled as part of surgical articulation system 10 in the blister pack.

Figure 19:
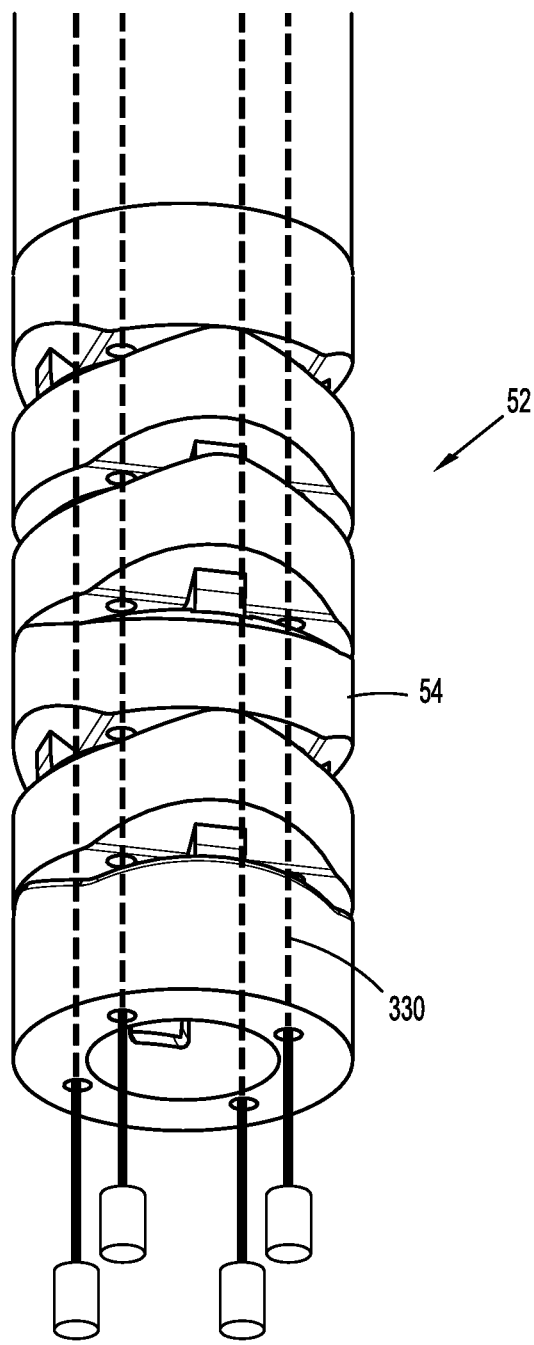
FIG. 19 is a perspective view of the articulation section of the surgical articulation system of FIG. 1.

Referring now to FIG. 19, articulatable member 50 includes an articulation section 52. Cables 330 extend from articulation mechanism 30 to articulation section 52 and are attached to articulation section 52 such that upon rotation of one of rotating members 380 and 382, a respective bar member 340 or 342 rotates to pull one of cables 330 proximally and to allow another of cables 330 to move distally. When the one of bar members 340 and 342 pulls the one of cables 330 proximally, articulation section 52 is bent or articulated in a direction corresponding to the pulled cable 330. Proximal movement of one of cables 330 also results in the distal movement of the corresponding cable 330 secured to an opposite end of the bar member 340 or 342. Depending on the configuration of cables 330 the direction of articulation of articulation section 50 may correspond to the direction of rotation of one of rotating members 380 and 382. Articulation section 52 includes articulatable links 54 where each adjacent link 54 is rotationally offset about the longitudinal axis of the articulation section 52 and adapted to bend or articulate in a direction off axis to the longitudinal axis and transverse to the previous link 54.

During use, referring to FIGS. 9-12, a surgeon inserts end effector 60 and articulatable member 50 into an opening in tissue such as, for example, a natural orifice (mouth, vagina, anus, etc) or an opening. End effector 60 and articulatable member 50 may also be inserted into the opening in tissue through a surgical access portal or other device. Once inserted, the surgeon manipulates rotating member 380 in a first rotational direction about the longitudinal axis A-A to articulate articulatable section 52 in a first direction (e.g. when viewed from proximal toward distal, clockwise rotation of rotating member 380 may articulate articulatable section 52 to the right). Articulatable section 52 is articulated due to the motion of cables 330 where, for example, as a first cable 330 on one side of articulatable section 52 is pulled proximally by bar member 340, a second cable 330 on an opposite side of articulatable section 52 is allowed moved distally by bar member 340 by the same amount. The proximal movement of the first cable 330 and the distal movement of the second cable 330 allow the articulatable section 52 to bend in the direction of the first cable 330. The surgeon may alternatively rotate rotating member 380 in a second rotational direction about the longitudinal axis A-A opposite the first rotational direction to articulate articulatable section 52 in a direction opposite the first direction. The surgeon may also rotate rotating member 382 in the first rotational direction to articulate articulatable section 52 in a second direction transverse to the first direction and may rotate rotating member 382 in the second rotational direction to articulate articulatable section 52 in a direction opposite the second direction. Both rotating members 380 and 382 may be rotated at the same time to articulate articulatable section in any combination of the first and second directions. In this way articulatable section 52 may be articulating in any direction relative to a longitudinal axis of articulation member 50. Once end effector 60 is positioned in the desired position the surgeon may rotate knob 322 to rotate end effector 60 about a longitudinal axis of end effector 60. The surgeon may also actuate lever 22 of handle 20 to actuate end effector 60 to perform the surgical operation.

Referring now to FIGS. 15-18, an alternate embodiment is disclosed which is similar to the previous embodiment. For clarity only those features which are different will be described. In this embodiment articulation mechanism 1300 includes rotating members 1380 and 1382 which are generally the same as rotating members 380 and 382. Articulation mechanism 1300 also includes bar members 1340 and 1342 which are generally the same as bar members 340 and 342 except that instead of pulley openings 360, pulleys 362, pin openings 364 and pins 366, bar members 1340 and 1342 include a cable hole 1360 extending through each end portion 1344, 1346, 1348 and 1350. Each cable hole 1360 is adapted to receive one of cables 330 therethrough and to secure or attach one of cables 330 in the manner described above where, in this case, cables 330 are attached directly to bar members 1340 and 1342. In this embodiment spacing members 1400 have a single hole 1406 in each flange 1404 for the reception of cables 330 therethrough. Alternatively spacing members 400 may still be used and bar members 1340 and 1342 may include more than one cable hole 1360 on each end portion 1344, 1346, 1348, 1350 such that cables 330 loop through the more than one cable hole 1360 and are secured to spacing members 400 as described above.

Although the present disclosure has been described with respect to preferred embodiments, it will be readily apparent, to those having ordinary skill in the art that changes and modifications may be made thereto without departing from the spirit or scope of the subject apparatus.

The invention claimed is:

1. A surgical articulation system comprising:
a handle assembly;
an articulation mechanism extending from the handle assembly comprising:
a housing defining a longitudinal axis and including:
a first slot extending at least partially through the housing; and
a second slot extending at least partially through the housing and offset from the first slot; and
a first bar member inserted into the first slot and configured to rotate within the first slot about a first axis that is transverse to the longitudinal axis of the housing;
a second bar member inserted into the second slot and configured to rotate within the second slot about a second axis, the first axis being transverse to the second axis, wherein the first bar member and the second bar member are independently rotatable; and a first rotating member configured to rotate about the longitudinal axis of the housing to perform a rotational movement, wherein the first rotating member is configured to rotate the first bar member about the first axis by the rotational movement of the first rotating member;

an elongate member extending from the articulation mechanism along the longitudinal axis of the housing and including at least one articulatable section, wherein the first bar member and the second bar member are configured to articulate the articulatable section through a plurality of cables;

the plurality of cables extending between the at least one articulatable section and each of the first and second bar members;

and an end effector extending from the elongate member and being actuatable by the handle assembly.

2. The surgical articulation system according to claim 1, wherein the rotating member defines a passageway for the reception of the housing, the passageway defining an internal thread configured to engage at least one end portion of the first bar member and to cause the rotation of the first bar member about the first axis by the rotational movement of the first rotating member.

3. The surgical articulation system according to claim 1, wherein the first rotating member is configured to articulate the articulatable section in two opposing directions by respectively rotating the first bar member in opposing rotational directions.

4. The surgical articulation system of claim 1, wherein each bar member includes a pulley inserted into a channel defined therein for engaging one cable of the plurality of cables.

5. The surgical articulation system of claim 1, wherein at least one end portion of each bar member defines a tapered section.

6. The surgical articulation system of claim 2, wherein at least one end portion of each bar member includes a rounded tip configured to engage the internal thread of the rotating member.

7. The surgical articulation system of claim 1, further comprising a second rotating member rotatable about the longitudinal axis of the housing and operably coupled to the second bar member, wherein the second rotating member is configured to rotate the second bar member about the second axis by a rotational movement of the second rotating member.

8. The surgical articulation system of claim 1, wherein the first slot is disposed distally from a proximal end of the housing, and the second slot is disposed distally from the first slot.

9. The surgical articulation system of claim 1, wherein the handle assembly includes a grip and a lever.

* * * * *